(12) United States Patent
Nicolo

(10) Patent No.: US 9,636,203 B2
(45) Date of Patent: May 2, 2017

(54) METHOD AND APPARATUS OF TENSION FREE INGUINAL HERNIA REPAIR RECONSTRUCTING PHYSIOLOGY USING INGUINAL HERNIA PROSTHETIC HAVING LATERAL NON-ENCIRCLING CORD LOCATING STRUCTURE

(76) Inventor: Enrico Nicolo, Jefferson Hills, PA (US)

( * ) Notice: Subject to any disclaimer, the term of this patent is extended or adjusted under 35 U.S.C. 154(b) by 1205 days.

(21) Appl. No.: 13/078,338

(22) Filed: Apr. 1, 2011

(65) Prior Publication Data
US 2012/0078274 A1 Mar. 29, 2012

Related U.S. Application Data

(63) Continuation of application No. PCT/US2009/059257, filed on Oct. 1, 2009.

(60) Provisional application No. 61/101,702, filed on Oct. 1, 2008.

(51) Int. Cl.
*A61F 2/02* (2006.01)
*A61F 2/00* (2006.01)

(52) U.S. Cl.
CPC .................................. *A61F 2/0063* (2013.01)

(58) Field of Classification Search
CPC ...................................................... A61F 2/0063
USPC ........... 606/151, 213–216; 623/23.72, 11.11, 623/13.11; 600/37
See application file for complete search history.

(56) References Cited

U.S. PATENT DOCUMENTS

| | | | |
|---|---|---|---|
| 2,671,444 A | 3/1954 | Pease, Jr. | |
| 4,769,038 A * | 9/1988 | Bendavid et al. | 623/13.11 |
| 5,593,441 A | 1/1997 | Lichtenstein et al. | |
| 5,697,978 A | 12/1997 | Sgro | |
| 5,716,409 A | 2/1998 | Debbas | |
| 5,813,975 A * | 9/1998 | Valenti | 600/37 |
| 5,824,082 A | 10/1998 | Brown | |
| 6,174,320 B1 | 1/2001 | Kugel et al. | |
| 6,497,650 B1 * | 12/2002 | Nicolo | 600/37 |
| 6,565,580 B1 | 5/2003 | Beretta | |
| 6,610,006 B1 * | 8/2003 | Amid et al. | 600/37 |

(Continued)

FOREIGN PATENT DOCUMENTS

EP 0719527 A1 7/1996
WO WO 96/14805 2/1996

(Continued)

*Primary Examiner* — Gregory Anderson
*Assistant Examiner* — Christina Lauer
(74) *Attorney, Agent, or Firm* — Blynn L. Shideler; Krisanne Shideler; BLK Law Group

(57) ABSTRACT

An inguinal hernia prosthesis includes a cord locating structure that provides cord protecting functions. The cord locating structure, which may be a semi-circular or other shaped recess positioned along a longitudinal peripheral edge of the prosthesis, is designed to only surround a portion of the cord, e.g. less than 180 or preferably 120 degrees, with the remaining cord circumference being positioned by the element against appropriate muscle tissue. The cord locating structure may be referenced as a non-encircling lateral cord locating structure. The prosthetic: provides tension free repair; minimizes cord damage through tissue ingrowth/strangulation effects, inadvertent suturing through the cord structure, and abrasion with the prosthetic; and minimizes size of prosthetic used in the repair; and is configured to reconstitutes the pre-hernia muscle physiology.

20 Claims, 1 Drawing Sheet

(56) References Cited

U.S. PATENT DOCUMENTS

| | | |
|---|---|---|
| 6,652,595 B1 | 11/2003 | Nicolo |
| 6,736,823 B2 | 5/2004 | Darois et al. |
| 7,094,261 B2 | 8/2006 | Zotti et al. |
| 7,156,804 B2 | 1/2007 | Nicolo |
| 2001/0049538 A1 | 12/2001 | Trabucco |
| 2002/0052654 A1 | 5/2002 | Darois et al. |
| 2003/0078602 A1 | 4/2003 | Rousseau |
| 2003/0212460 A1 | 11/2003 | Darois et al. |
| 2004/0068275 A1 | 4/2004 | Ramshaw et al. |
| 2005/0192600 A1 | 9/2005 | Nicolo et al. |
| 2006/0064175 A1 | 3/2006 | Pelissier et al. |
| 2007/0032881 A1 | 2/2007 | Browning |

FOREIGN PATENT DOCUMENTS

| | | |
|---|---|---|
| WO | WO 97/35533 | 10/1997 |
| WO | WO 2010/039978 | 4/2010 |

* cited by examiner

METHOD AND APPARATUS OF TENSION FREE INGUINAL HERNIA REPAIR RECONSTRUCTING PHYSIOLOGY USING INGUINAL HERNIA PROSTHETIC HAVING LATERAL NON-ENCIRCLING CORD LOCATING STRUCTURE

RELATED APPLICATIONS

This application is a continuation of International Patent Application Serial Number PCT/US2009/059257 filed Oct. 1, 2009. International Patent Application Serial Number PCT/US2009/059257 claims priority to U.S. provisional patent application Ser. No. 61/101,702 filed Oct. 1, 2008, entitled "Method and Apparatus for Tension Free Inguinal Hernia Repair using Inguinal Hernia Prosthetic having Lateral Non-encircling Cord Locating Structure"

BACKGROUND OF THE INVENTION

Field of the Invention

The present invention relates to inguinal hernia repair, and more particularly to an inguinal hernia prosthetic having lateral non-encircling cord locating structure which is configured to constitute the physiologic structure prior to the hernia defect.

Background Information

Hernias have plagued humans throughout recorded history, and descriptions of hernia reduction date back to Hammurabi of Babylon and early Egyptian writings.

Inguinal hernias are generally described as protrusions of abdominal cavity contents through the inguinal canal. The inguinal canal is a passage in the anterior abdominal wall which conveys the spermatic cord, in men, and the round ligament, in women. The inguinal canal is larger and more prominent in men. The spermatic cord is the cord-like structure in males formed by the vas deferens and surrounding tissue (including nerves and testicular blood supply) that run from the abdomen down to each testicle.

Inguinal hernias are very common. It has been estimated that 5% of the population will develop an abdominal wall hernia at some time in their lifetime. The repair of inguinal hernias is one of the most frequently performed surgical operations. There are two types of inguinal hernias, direct and indirect. Direct inguinal hernias occur when abdominal contents extend through a weak point in the fascia of the abdominal wall and into the inguinal canal. Indirect inguinal hernias occur when abdominal contents protrude through the deep inguinal ring.

Most patients with inguinal hernias elect surgery to repair inguinal hernias and avoid the possibility of a strangulated hernia. The procedure to repair a hernia involves, basically, pushing the piece of intestine back into place and surgically repairing the abdominal wall so the intestine cannot push through again. Hernia surgery, called herniorrhaphy or hernioplasty, can be an open procedure or a laparoscopic procedure.

Original hernia surgery utilized the patients existing tissue to repair the defect and this is now known as "pure tissue" repair of a hernia defect. Edwardo Bassini in 1888 posted a milestone in the history of not only hernia surgery, but of all surgery, when he reported a reduction in the recurrence rate to about 10% (from a conservative estimated 30-40% rate earlier) with his operation which was a unique combination of understanding of anatomy and application of surgical thinking and technique. This 10% recurrence rate was achieved at a period without antibiotics, primitive anesthesia and at a time when patients often suffered with their hernia until they reached a giant size before submitting to surgery.

Bassini's operation epitomized the essential steps for an ideal tissue repair. He opened the external oblique aponeurosis through the external ring, then resected the cremasteric fascia to expose the spermatic cord. He then divided the canal's posterior wall to expose the preperitoneal space and did a high dissection and ligation of the peritoneal sac in the iliac fossa. Bassini then reconstructed the canal's posterior wall in three layers. He approximated the medial tissues, including the internal oblique muscle, transversus abdominus muscle and transversalis fascia to the shelving edge of the inguinal ligament with interrupted sutures. He then placed the cord against that newly constructed wall and closed the external oblique aponeurosis over it, thereby restoring the step-down effect of the canal and reforming the external inguinal ring.

For well over a century, Bassini's pure tissue repair procedures, with several modifications (e.g. Halsted, McVay, Tanner, Shouldice . . . ) have helped preserve useful life in hundreds of thousands cases. While most modern "herniologists" view pure tissue repair as a method to be discarded, its very economical cost structure makes it, even today, the commonest form of hernia repair in most part of the developing world.

Hernia repair prosthetics have been developed, also called hernia patches and hernia meshes, for use in what is known as a tension free repair of a hernia defect. The prosthetic generally bridges the gap forming the defect and the patient's tissue is not "stretched" over the defect, thus allowing the tissue to remain "tension free". The tension-free mesh repair is invariably linked to Lichtenstein whose work and progress over two decades culminated in the tension free Lichtenstein repair. The "tension free" prosthetic hernia repair procedures have evidenced a significant reduction in reoccurrence of hernias over the pure tissue repair, an minimized recovery period, and a decrease in post operative patient pain and have thus become the most popular repair for hernia defects.

Numerous surgically implantable hernia repair prosthetics have been proposed, such a polypropylene mesh patches for the repair of inguinal, and other abdominal wall, hernias. These prosthetics are generally intended for permanent placement within a patient's body space.

U.S. Pat. No. 5,593,441 is a representative example of one hernia prosthesis and discloses ventral hernia and/or chest wall reconstruction prosthesis that is a polypropylene mesh covered with an adhesion resistant barrier, such as a sheet of expanded PTFE. In the repair of ventral hernias and in chest wall reconstruction, the composite is positioned with the barrier relative to the region of potential adhesion, such as the abdominal viscera.

International Publication No. WO 97/35533 proposed a universal composite prosthesis in which one side of a layer of mesh material is completely covered with a layer of barrier material. The mesh material promotes biological tissue in-growth while the barrier material retards biological tissue adherence thereto.

U.S. Pat. No. 2,671,444 to Pease discloses a non-metallic mesh surgical insert for hernia repair. The non-metallic mesh surgical insert is preferably made from a polyethylene mesh.

Inguinal hernias are commonly repaired using a sheet of mesh fabric, such as polypropylene or PTFE (polytetra-flouroethylene), which may be trimmed, as necessary, to match the particular size and shape of the inguinal floor. A slit, or keyhole, is preformed or made by the surgeon from the lateral end of the mesh opposite the medial corner of the inguinal canal toward the medial end of the mesh to form a pair of lateral tails that are separated to receive the spermatic cord there between. The tails may then be overlapped to encircle the cord and reinforce the internal ring.

U.S. Pat. No. 5,716,409 discloses an inguinal hernia repair sheet for use in surgery that includes an opening to receive a spermatic cord and a passageway designed to allow the opening to fit around the spermatic cord.

U.S. Pat. No. 4,769,038 discloses a plug for the repair of a femoral hernia. The plug or prosthesis has multiple layers or panels and fits around the spermatic cord.

PCT Application No. WO 96/14805 discloses a double layer prosthesis that is applied to a patient with an inguinal hernia. See also U.S. Pat. No. 5,813,975 for an example of a keyhole type inguinal hernia mesh.

European Patent No. 0719527A1 discloses dual layer prosthesis for an indirect inguinal hernia. The first layer is a solid sheet while the second layer has a center hole and a strip cut towards the center hole.

U.S. published patent application No. 2001-0049538 is a set of plugs and hernia mesh pieces for a particular surgical technique.

U.S. Pat. No. 6,174,320 discloses a suture-less hernia repair patch having a slit for receiving a patient's chord structure when placing a patch in a patient for hernia repair.

U.S. published patent application 2005-0192600 discloses a suture-less, tension free, one-piece, double layer, inguinal hernia repair prosthetic is preferably formed of a single piece or sheet of repair fabric, such as polypropylene mesh, PTFE mesh, biologic material, or combinations thereof. The prosthetic sheet preferably includes a fold line dividing the sheet into two general halves. Each prosthetic half of the prosthetic sheet is preferably shaped generally to fit within the inguinal canal. Each prosthetic half of the sheet includes an opening in the inner portion of the sheet and a slit extending to the peripheral portion of the prosthetic half. The slits extend to generally opposite side of the prosthetic. Each opening is adapted to receive a patient's spermatic cord structure there through.

U.S. published patent application 2004-0068275 discloses a complex hernia prosthetic. This reinforcement comprises a first piece and a second piece which are assembled with one another, said first piece comprising a longitudinal edge of corrugated shape, level with which said second piece is fixed. In this reinforcement, said first piece comprises a cutout forming a zone, located at a distance from said longitudinal edge, for the spermatic cord to pass through it, and comprises a flap which is joined to it and is dimensioned so as to extend close to said longitudinal edge and to broadly cover the zone of said first piece extending between said longitudinal edge and said passage zone, this flap being raised in relation to said first piece in order to engage the spermatic cord between said first piece and itself and being foldable against said first piece in order to hold this cord between this first piece and itself.

U.S. Pat. No. 6,565,580 discloses an inguinal hernia correcting prosthesis having an upper layer and a lower layer connected to each other by a flexible band, the flexible band having a first end fixed to the upper layer next to a recess provided on an edge of the upper layer, and a second end fixed next to a hole provided in the lower layer and connected by a cut to an external edge of the lower layer, the hole being axially aligned with the band and the recess.

U.S. Pat. Nos. 7,154,804 and 6,497,650 disclose prosthesis for repairing a tissue or muscle wall defect. The prosthesis comprises a layer of repair fabric having first and second and an edge that extends between the first and second surfaces. The prosthesis also includes a barrier that is inhibits the formation of adhesions with adjacent tissues and organs. The barrier may overlap a portion of the first and second surfaces. The barrier may be formed separate from and attached to the layer of repair fabric to permanently cover a portion of the edge. The repair fabric may be formed from a material which is susceptible to the formation of adhesions with sensitive tissue and organs. The cord protector may be formed from material which inhibits the formation of adhesions with sensitive tissue and organs. The barrier may overlie a portion of at least one of the first and second surfaces of the repair fabric.

These U.S. Patents and published patent applications are incorporated herein by reference in their entirety. Some of these earlier hernia repair prosthetics are complex. Several use a plug or a locating member to fit within the hernia defect itself. When considering the hernia defect as a defect in the muscle, the problems with contemporary plug or patch prosthesis are easier to highlight. In both situations of using conventional patch prosthesis or plug hernia prosthesis (somewhat less common) the "hernia defect" is conventionally considered as "cured" with the application of the hernia prosthesis as the hernia defect is covered or filled. However in both situations of using conventional patch prosthesis or plug hernia prosthesis the "muscle defect" is left untouched. The "defect" remains, but the hernia is prevented through the prosthetic. In fact with plug type repairs the "muscle defect" is actually increased as the plug expands the muscle defect in filling the hole. Consequently in this sense these existing prosthetics fail to reconstruct the pre-hernia physiology.

Although these medical advances are acknowledged for their usefulness and success in reducing the incidence of reoccurrence of the hernia, there remains a need or needs for more improvements in the surgical repair of inguinal hernias, and in attempts to reconstitute the pre-hernia physiology. Further, there is a need for an improved implantable inguinal hernia repair prosthetic having structure to facilitate the repair and to protect the cord structures, namely the spermatic cord, from damage.

SUMMARY OF THE INVENTION

One aspect of this invention is directed to an inguinal hernia prosthesis with a cord locating structure that provides cord protecting functions. The cord locating structure, which may be a semi-circular or other shaped recess positioned along a longitudinal peripheral edge of the prosthesis, is designed to only surround a portion of the cord, e.g. less than 180 degrees, and more preferably less than 120 degrees, with the remaining cord circumference being positioned by the element against appropriate muscle tissue. The cord locating structure may be referenced as a non-encircling lateral cord locating structure.

The cord locating structure preferably includes edge protection, wherein the cord engaging edge will, preferably, be formed of, or covered with, appropriate material that avoids detrimental interference with the cord structure. These materials include biologic materials, bio-absorbable materials, PTFE and other materials that exhibit less tissue in-growth than polypropylene mesh. Edge protection is described in U.S. Pat. No. 6,497,650 which is incorporated herein by reference.

The present invention contemplates a narrow aspect pre-shaped prosthetic that minimizes the amount of prosthetic material used in repair, while still providing tension free repair.

The term narrow aspect within the meaning of this application references that the length to width ratio of the prosthesis is at least 2. However, another aspect of this invention is providing a "semi-pre-shaped" structure that allows the surgeon to trim one side to the desired shape for use, while still leaving the edge protected sidewall with cord locating structure intact (untrimmed). The narrow aspect prosthetic according to the invention is used to proximate the muscle tissue to the ligament, through the prosthetic, rather than have the prosthetic overlay the muscle and ligament as with the majority of prior art prosthetics.

One object of the present invention is to reconstruct the pre-hernia physiology through a proximation of the muscle side to the ligament side with the "narrow aspect" prosthesis. The prosthesis is selected to provide the tension free aspects of the repair as opposed to a pure tissue repair, but the prosthesis maintained as a minimum component. Further, prosthesis shrinkage over time, if any, following surgery will act to further reconstitute the pre-hernia physiology.

The prosthetic according to the present invention: (1) maintains the advantages of a tension free prosthetic hernia repair with the associated low incidence of recurrence, (2) minimizes the likelihood of cord damage (i) through tissue in-growth/strangulation effects after hernia repair, (ii) through inadvertent suturing through the cord structure during hernia repair as the cord is precisely located, and (iii) through abrasion with the prosthetic due to the edge protection and non-encircling structure, and (3) may be used to minimize size of prosthetic material implemented in the repair to reconstitute pre-hernia physiology.

It is noted that, as used in this specification and the appended claims, the singular forms "a," "an," and "the" include plural referents unless expressly and unequivocally limited to one referent. The features that characterize the present invention are pointed out with particularity in the claims which are part of this disclosure. These and other features of the invention, its operating advantages and the specific objects obtained by its use will be more fully understood from the following detailed description and the operating examples.

These and other advantages are described in the brief description of the preferred embodiments in which like reference numeral represent like elements throughout.

DESCRIPTION OF THE PREFERRED EMBODIMENTS

Figure 1:
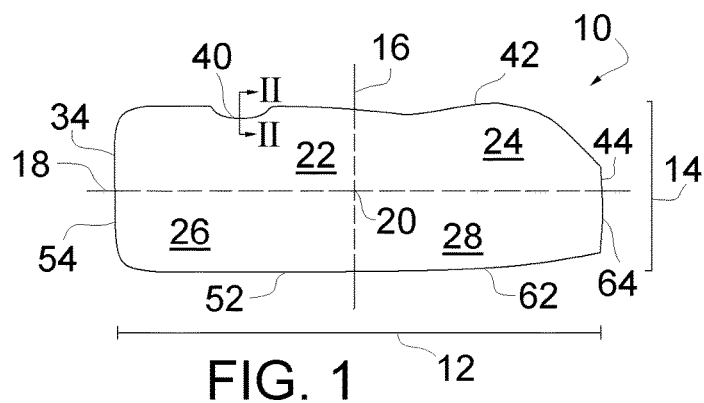
FIG. 1 is schematic plan view of narrow aspect pre-shaped inguinal hernia prosthesis with lateral cord locating structure in accordance with one embodiment of the present invention.

FIG. 1 is schematic plan view of narrow aspect pre-shaped inguinal hernia prosthesis 10 in accordance with one embodiment of the present invention. The prosthesis 10 has a longitudinal length 12 and a width 14. The phrase "narrow aspect" according to the present application references that the length to width ratio of the prosthesis is at least 2. Further, in the present invention the length to width ratio of the prosthesis may be at least 2.5, and may be at least 3. Specifically the illustrated width is 3 cm and the length is 10 cm. A 10 cm by 4 cm prosthesis is also an effective sizing for a pre-shaped, narrow aspect prosthesis 10 according to the present invention.

As will be discussed in detail below, the narrow aspect of the present invention allows the prosthesis 10 to bridge the hernia defect and provide the tension free repair of the hernia defect that is desirable and effectively a standard of care in the art. However the narrow aspect minimizes the amount of material used in the hernia repair and avoids excessive overlap of material as is commonly found in prior art designs.

The use of excessive prosthetic material in hernia repair is not believed to detrimentally affect the reoccurrence rate for the hernia itself (indeed the hernia will be "fixed" with the use of large oversized patches), but use of excessive material is believed to increase the likelihood of other complications due to the interaction of the prosthesis and the body tissue and the use of excessive hernia prosthesis material does not align with best surgical practices.

The narrow aspect prosthesis 10 serves to proximate the muscle to the ligament structure, in a manner analogous to pure tissue repair, but while still maintaining a tension free approach to provide for both repair of the inguinal hernia and reconstitution of the pre-hernia muscle physiology.

An understanding of the inguinal canal is helpful in describing inguinal hernia repair, in general, and certainly in describing repair with a narrow aspect prosthesis 10. The inguinal canal is situated just above the medial half of the inguinal ligament and is oblique directed downwards, forwards and medially and about 4 cm in length. The inguinal canal can be visualized roughly as a cylinder, stretching from the deep inguinal ring to the superficial inguinal ring. The deep inguinal ring, also called internal inguinal ring, is generally of an oval form, with the long axis of the oval being vertical and the deep inguinal ring varies in size in different subjects, and is much larger in the male than in the female. The superficial inguinal ring, also called the external inguinal ring, or the subcutaneous ring is a triangular opening situated 1 centimeter above and lateral to the pubic tubercle or pubic spine. Defining the boundaries of the inguinal canal between the internal and external rings are four "sides" usually called the "anterior wall", "posterior wall", "roof", and "floor."

The roof or superior wall of the inguinal canal includes the internal oblique muscle and the transversus abdominis muscle, also known as the transversalis muscle and transverse abdominal muscle. In general this can be referenced as the muscle tissue herein.

The posterior wall of the inguinal canal includes the transversalis fascia, or transverse fascia which is a thin aponeurotic membrane, and the conjoint tendon in the medial third of the inguinal canal, also called the inguinal aponeurotic falx formed from the conjoin tendons of the internal oblique and transverse abdominis muscles.

The floor or inferior wall includes the inguinal ligament, the lacunar ligament in the medial third of the inguinal canal and the iliopubic tract in the lateral third of the inguinal canal. In general this side can be referenced as the ligament portion of the inguinal canal.

The anterior wall includes the aponeurosis of the external oblique, and the aponeurosis of internal oblique in the lateral third of the inguinal canal.

The prosthesis 10 includes a longitudinal median 16 and a width median 18 that defines a center point 20 for the prosthesis 10. The medians 16 and 18 divide the prosthesis 10 into an upper anterior quadrant 22, upper posterior quadrant 24, lower anterior quadrant 26 and lower posterior quadrant 28.

The upper anterior quadrant 22 is bounded by a generally longitudinally extending edge 32 of the prosthesis 10 and an edge 34 generally extending along the width of the prosthesis 10. The prosthesis 10 avoids sharp corners and includes a smooth transition between the edges 32 and 34. Further, each of the edges 32 and 34 is shaped to generally conform to the associated form of the inguinal canal.

A significant feature of the present invention is the provision of a cord locating structure 40 that provides cord protecting functions. The cord locating structure 40, which may be a semi-circular or other shaped recess positioned, along the longitudinal peripheral edge 32 of the prosthesis 10, is designed to only surround a portion of the cord. The structure 40 is configured to surround 180 degrees or less of the spermatic cord structure, more preferably 120 degrees or less of the cord structure, with the remaining cord circumference being positioned by the structure 40 against appropriate muscle tissue in the inguinal canal. As noted below the purpose of the cord locating structure 40 is to position the cord, mainly during hernia repair, and protect the cord.

Testicular ischaemia and posterior atrophy have been reported to occur following primary inguinal hernia repair (some reports at around 0.5%), although these complications are more common after surgery for recurrent inguinal hernia with an incidence with reports of up to 5% occurrence. Some have reported the incidence appears to be less in patients with laparoscopic inguinal hernia repair. It has been reported that testicular atrophy is a complication from inguinal surgery that has a heighten risk of patient dissatisfaction and corresponding legal disputes. Additionally a thickened spermatic cord has been reported as a relatively frequent finding in patients with inguinal hernia repair when studied in the immediate post-operative period. The cord locating structure 40 of the present invention will help minimize these medical complications as well.

The cord locating structure 40 may be referenced as a non-encircling lateral cord locating structure. The term lateral in reference to structure on a prosthesis 10 within the meaning of the present application will reference structure extending to a longitudinally extending side edge (e.g. 32, 42, 52 and 62, described below) of the prosthesis 10. The term non-encircling indicates that the structure 40 is intended to be adjacent only a portion of the periphery of the spermatic cord once the prosthesis 10 is in place.

Figure 4A:
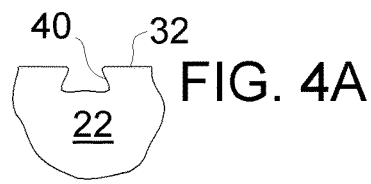
FIGS. 4A-G are schematic plan views of alternative lateral cord locating structures of the prosthesis of FIG. 1.
Figure 4B:
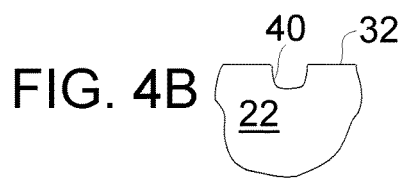
Figure 4C:
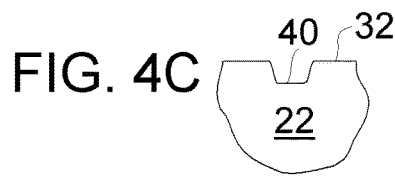
Figure 4D:
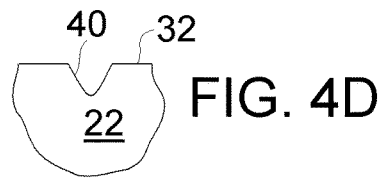
Figure 4E:
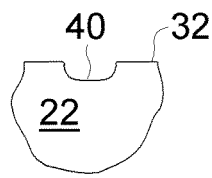
Figure 4G:
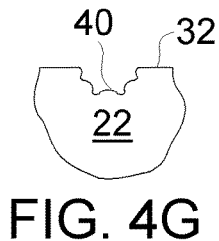
Figure 4F:
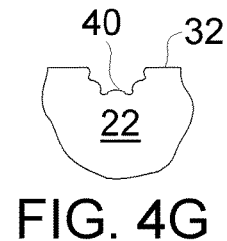

The structure 40 can be formed as a recess of a number of shapes which also avoids sharp corners, and will include radius transitions as shown. For example the recess forming the structure 40 may be a semi-circle that extends less than 180 degrees about the cord structure as shown in FIG. 1, and about 120 degrees as shown is contemplated within the scope of the present invention. Alternatively, FIG. 4A illustrates a rounded trapezoidal type recess for structure 40, FIG. 4B illustrates a recess for structure 40 with a number of flat portions (a polygonal type recess with rounded transitions), FIG. 4C illustrates a rounded trapezoidal type recess for structure 40 with the sides diverging, 4D illustrates a rounded triangular type or "V" type recess for structure 40, FIG. 4E illustrates an elongated oval or ellipse type shape forming the recess for structure 40, FIG. 4E illustrates an elongated groove forming the recess for structure 40, and FIG. 4G illustrates a recess forming structure 40 with a plurality of projections that will space the cord from the edge of the structure 40. These are merely illustrative of the numerous particular shapes that are possible for the recess forming the structure 40 according to the present invention.

The structure 40 is intended to receive at least part of the cord and thereby precisely locate the cord, without completely surrounding the cord. The location of the cord itself in the specified location helps to protect the cord as the cord will be positioned in a location that will be avoided with fasteners (sutures or the like). Damaging the cord structure with an inadvertent suture, staple or the like, is one concern regarding the protection of the cord structure in hernia repair procedures. The non-encircling nature of structure 40 avoids the possibility of strangulation of the cord structure due to the tissue and prosthesis 10 interactions. The cord locating structure 40 is believed to minimize the likelihood of tissue ingrowth into the cord that could damage the cord, through the non-encircling configuration. Additionally the structure 40 is located on the prosthesis 10 to best locate the cord relative to the prosthesis 10 and the physiology.

The upper posterior quadrant 24 is bounded by a generally longitudinally extending edge 42 of the prosthesis 10 and an edge 44 generally extending along the width of the prosthesis 10. The prosthesis 10 includes a smooth transition between the edges 42 and 44. Further, each of the edges 42 and 44 is shaped to generally conform to the associated form of the inguinal canal. The edge 42 may include a "bump out" shape that will conform to the natural shape of the inguinal canal.

The lower anterior quadrant 26 is similarly bounded by a generally longitudinally extending edge 52 of the prosthesis 10 and an edge 54 generally extending along the width of the prosthesis 10. The lower posterior quadrant 28 is bounded by a generally longitudinally extending edge 62 of the prosthesis 10 and an edge 64 generally extending along the width of the prosthesis 10. The prosthesis 10 includes a smooth transition between the edges 52 and 54, and 62 and 64. Further, each of the edges 52 and 54, 62 and 64 are shaped to generally conform to the associated form of the inguinal canal.

The cord locating structure 40 preferably includes edge protection, wherein the cord engaging edge will, preferably, be formed of, or covered with, appropriate material that avoids detrimental interference with the cord structure. These materials include biologic materials, bio-absorbable materials, PTFE and other materials that exhibit less tissue in-growth than polypropylene mesh. The edge protection is desired to prevent abrasion type damage to the cord structure through interaction of the cord structure and the edge of the prosthesis 10.

Figure 2A:
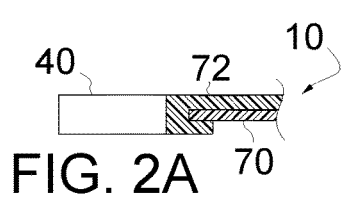
FIG. 2A is a sectional view of a protected side edge at the lateral cord locating structure of the prosthesis of FIG. 1.
Figure 2B:
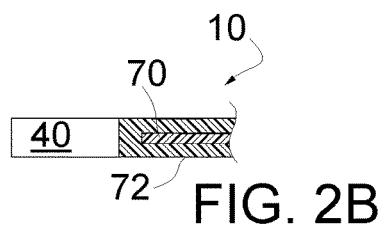
FIG. 2B is a sectional view of a protected side edge at the lateral cord locating structure of a modified prosthesis of FIG. 1.

FIGS. 2A and 2B illustrate embodiments of the structure 40 with edge protection for the prosthesis 10 for inguinal hernia repairs. The prosthesis 10 includes a layer of mesh fabric 70 and a barrier layer or protecting layer 72 at least along the edge. As illustrated in FIG. 2A, the barrier layer 72, or the cord protector layer, may limited to overlying portions of the fabric 70 in close proximity to the opening or recess forming the structure 40. This configuration would be expected to increase tissue adhesion to the prosthesis 10 in other areas of the prosthesis 10 not covered with the barrier layer 72, while limiting cord adhesion in the vicinity of the opening due to the layer 72. Further details of this type of multilayer edge protection can be found in U.S. Pat. Nos. 7,154,804 and 6,497,650 that are incorporated herein by reference in their entirety. Alternatively, the fabric 70 may be completely encapsulated in the layer 72 as schematically shown in FIG. 2B. The encapsulated embodiment of FIG. 2B will generally use the fabric 70 for the structural integrity of the prosthesis and the layer 72 for its improved tissue interaction with regard to cord protection and the like.

In one embodiment, the layer of repair fabric 70 is formed of a polyolefin material, such as a sheet of knitted polypropylene monofilament mesh fabric. One example of a suitable material is BARD MESH Bard "soft Mesh" (a large pore monofilament polypropylene that has approximately 60% less weight than traditional polypropylene mesh, both available from C.R. Bard, Inc. When implanted, the polypropylene mesh promotes rapid tissue ingrowth into and around the mesh structure.

Other surgical materials which are suitable for tissue reinforcement and defect closure may be utilized for fabric 70 including PROLENE, SOFT TISSUE PATCH (microporous ePTFE), SURGIPRO, TRELEX, ATRIUM and MERSELENE. Polyethylene may also form an acceptable polyolefin material for the layer 70. Absorbable materials, including polyglactin (VICRYL) and polyglycolic acid (DEXON), also may be suitable. It also is contemplated that the mesh fabric 70 may be formed from multifilament yarns and that woven, molded and other suitable methods of forming prosthetic mesh materials may be employed.

In one embodiment, the barrier layer 72 is formed from a fluoropolymer material such as polytetrafluoroethylene (PTFE). One example of a suitable material is a sheet of expanded polytetrafluoroethylene (ePTFE), such as GORE-TEX available from W.L. Gore & Associates, Inc., having a pore size (submicronal) that discourages tissue ingrowth and adhesion.

Fluorinated ethylene propylene (FEP), tetrafluoroethylene (TFE) and ethylene tetrafluoroethylene (ETFE) are other acceptable fluoropolymers for forming the barrier layer 72. A representative and non-limiting sampling of other suitable barrier materials includes silicone elastomer, such as SILASTIC Rx Medical Grade Sheeting (Platinum Cured) distributed by Dow Corning Corporation, TEFLON mesh, and microporous polypropylene sheeting (CELGARD). It is also contemplated that a polyethylene terephthalate, such as DACRON and MYLAR, may be employed as a barrier material.

Autogenous, heterogenous and xenogeneic tissue also are contemplated for use as the barrier layer 72 including, for example, pericardium and small intestine sub-mucosa. Absorbable materials, such as oxidized, regenerated cellulose (Intercede (TC7)) may be employed for some applications. It is to be appreciated that any suitable adhesion resistant materials may be used as would be apparent to one of skill in the art. See also U.S. Pat. Nos. 5,593,441, 5,725,577 and 5,743,917 for composite materials structures for hernia repair prosthesis. These patents are incorporated herein by reference.

The barrier materials described above could also be used WITHOUT the substrate that is fabric 70, provided these materials are formed structurally sufficiently to form hernia prosthesis 10. For example a barrier material may be provided and may include surface treatment (e.g. roughened) on selected portions thereof to promote tissue ingrowth. The advantage of the pre-shaped prosthesis 10 of the present invention is that it is known generally where the various portions of the prosthesis will lie in situ and can be formed accordingly. A preformed prosthesis can decrease operative time, which is at a premium.

Another embodiment of the present invention is to provide a semi-pre-shaped prosthesis 10. In this embodiment there is additional width and length provided to the prosthesis 10 as manufactured, however it is still believed to be a narrow aspect prosthesis. The edge protection described above will maintain along at least one edge 32, and possibly 42. The surgeon, in use, will only trim down the perimeter of the prosthesis 10 along the lower quadrants 26 and 28. In this manner the edge protection for the cord structure 40 is maintained even if the surgeon trims several sides. The surgeon can trim other portions of the prosthesis 10 as desired without effecting the cord protection offered by the edge protection as long as the structure 40 is not trimmed.

Figure 3A:
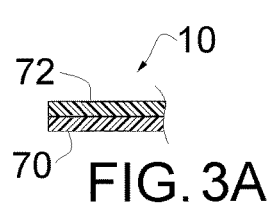
FIGS. 3A and 3B are sectional views of the formation of a protected side edge of a modified prosthesis of FIG. 1.
Figure 3B:
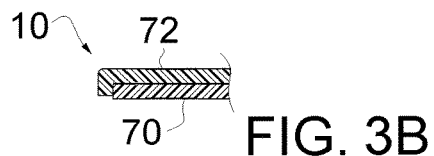

FIGS. 3A and 3B illustrate an edge protection concept that allows complete edge protection around the entire prosthesis 10 (whether trimmed or not). In this embodiment the barrier layer 72 is formed of a material adapted to swell to a sufficient extent to cover the edge. FIG. 3A illustrates the pre-swelled orientation of the structures. After the surgeon trims the prosthesis 10 as desired, the entire prosthesis 10 is soaked in appropriate biologic compatible fluid (e.g. saline) for a period of time (5-10 minutes) to allow the layer 72 to swell. In the expanded state, as shown in FIG. 3B the layer 72 protects the edge of the prosthesis 10. In this manner the prosthesis 10 can be supplied to the surgeon in any format and he can trim and form on site in response to the particular desired shape, and the final prosthesis 10 can include complete edge protection around the entire prosthesis 10. The edge protection is particularly advantageous for the cord structure, but the abrasive potential of the edge of a prosthesis 10 can be of concern to tissue other than the cord structure.

The prosthesis 10 can be used with open or laparoscopic repair procedures. Further the prosthesis 10 is believed to provide best performance with secure fastening of the prosthesis 10 into position with sutures or the like.

A further modification of the present invention is to incorporate a three dimensional shape to the pre-shaped prosthesis 10 of the present invention. Generally this would be the inclusion of some concavity to the device to better conform to the inguinal canal geometry. This embodiment is described as a 3-dimensional version of the prosthesis 10. In this embodiment it is contemplated that the prosthesis 10, in fabric 70, or another "memory layer", will be constructed to return to a desired three dimensional shape after implantation. Adding concavity will allow better conformation to the inguinal anatomy, but may provide a stiffer overall prosthesis, and thus edge protection is believed to be even more critical in such an embodiment. With a three dimensional shape it becomes possible to form prosthesis that avoids fixation (i.e. no sutures), similar to the BARD 3D MAX™ brand prosthesis, however minimal fixation is believed to be preferable to assure no migration and to act to proximate the muscle to the ligament to reconstruct pre-hernia physiology.

The use of the prosthesis 10 of the present invention is suitable for open procedures, and is particularly helpful for laparoscopic procedures. The prosthesis 10 of the present invention is suitable for method of repairing an inguinal hernia comprising the steps of using the hernia prosthetic 10 within the inguinal canal to proximate the muscle to the ligament structure while maintaining substantially tension free tissue to provide for both repair of the inguinal hernia and reconstitution of the pre-hernia muscle physiology. The method of repairing an inguinal hernia with the narrow aspect inguinal hernia prosthesis 10 includes using the cord locating structure 40 to only surround a portion of the cord with the remaining cord circumference being positioned by the cord locating structure against appropriate muscle tissue.

The preferred embodiments described above are illustrative of the present invention and not restrictive hereof. It will be obvious that various changes may be made to the present invention without departing from the spirit and scope of the invention. The precise scope of the present invention is defined by the appended claims and equivalents thereto.

What is claimed is:

1. A method of repairing an inguinal hernia in a patient comprising the steps of using a hernia prosthetic having a narrow aspect within the inguinal canal to proximate the muscle to the ligament structure while maintaining substantially tension free tissue to provide for both repair of the inguinal hernia and reconstitution of the pre-hernia muscle physiology wherein the step of using the hernia prosthetic having a narrow aspect within the inguinal canal includes placement of the patient's spermatic cord to the lateral side of the hernia prosthetic whereby the spermatic cord is not encircled by prosthetic material.

2. The method of repairing an inguinal hernia according to claim 1 wherein the narrow aspect inguinal hernia prosthesis includes a cord locating structure formed by a recess positioned along a longitudinal peripheral edge of the inguinal hernia prosthesis, wherein the prosthesis and the cord locating structure is configured to only surround a portion of the spermatic cord with the remaining spermatic cord circumference being positioned by the cord locating structure against the patient's muscle tissue.

3. The method of repairing an inguinal hernia according to claim 2 wherein the length to width ratio of the prosthesis is at least 2.5.

4. The method of repairing an inguinal hernia according to claim 2 wherein the length to width ratio of the prosthesis is at least 3.

5. The method of repairing an inguinal hernia according to claim 2 wherein the narrow aspect hernia prosthesis has a length of about 10 cm.

6. The method of repairing an inguinal hernia according to claim 2 wherein the narrow aspect inguinal hernia prosthesis includes a substrate and a protective layer at least at the edge of the cord locating structure.

7. The method of repairing an inguinal hernia according to claim 6 wherein the protective layer extends along at least one longitudinal side of the prosthesis.

8. The method of repairing an inguinal hernia according to claim 6 wherein the protective layer substantially encapsulates the substrate.

9. The method of repairing an inguinal hernia according to claim 2 wherein the prosthesis and the cord locating structure is configured to extend less than 180 degrees around the spermatic cord.

10. The method of repairing an inguinal hernia according to claim 2 wherein the prosthesis and the cord locating structure is configured to extend less than 120 degrees around the spermatic cord.

11. The method of repairing an inguinal hernia according to claim 10 wherein the length to width ratio of the prosthesis is at least 2.5 and wherein the cord locating structure is located on one side of a longitudinal median bisecting the prosthesis.

12. The method of repairing an inguinal hernia according to claim 11 wherein the narrow aspect inguinal hernia prosthesis includes a substrate and a protective layer at least at the edge of the cord locating structure.

13. An inguinal hernia prosthesis configured to repair an inguinal hernia of a patient, said inguinal hernia prosthesis including a cord locating structure formed by a recess positioned along a longitudinal peripheral edge of the prosthesis, wherein the prosthesis and the cord locating structure is configured to only surround a portion of the patient's spermatic cord with the remaining spermatic cord circumference being positioned by the cord locating structure against the patient's muscle tissue.

14. The inguinal hernia prosthesis according to claim 13 wherein the length to width ratio of the prosthesis is at least 2.5.

15. The inguinal hernia prosthesis according to claim 14 wherein the narrow aspect hernia prosthesis has a length of about 10 cm and wherein the cord locating structure is located on one side of a longitudinal median bisecting the prosthesis.

16. The inguinal hernia prosthesis according to claim 13 wherein the inguinal hernia prosthesis includes a substrate and a protective layer at least at the edge of the cord locating structure.

17. The inguinal hernia prosthesis according to claim 13 wherein the prosthesis and the cord locating structure is configured to extend less than 180 degrees around the spermatic cord.

18. The inguinal hernia prosthesis according to claim 13 wherein the prosthesis and the cord locating structure is configured to extend less than 120 degrees around the spermatic cord.

19. An inguinal hernia prosthetic configured to repair an inguinal hernia of a patient, said inguinal hernia prosthesis having a narrow aspect configured to proximate the muscle to the ligament structure while maintaining substantially tension free tissue to provide for both repair of the inguinal hernia and reconstitution of the pre-hernia muscle physiology, wherein the length to width ratio of the prosthesis is at least 3.0.

20. The inguinal hernia prosthetic according to claim 19 wherein the narrow aspect inguinal hernia prosthesis includes a cord locating structure formed by a recess positioned along a longitudinal peripheral edge of the prosthesis, wherein the prosthesis and the cord locating structure is configured to only surround a portion of the patient's spermatic cord with the remaining spermatic cord circumference being positioned by the cord locating structure against the patient's muscle tissue.

* * * * *